United States Patent [19]

Graves, Jr. et al.

[11] Patent Number: 4,737,411
[45] Date of Patent: Apr. 12, 1988

[54] CONTROLLED PORE SIZE CERAMICS PARTICULARLY FOR ORTHOPAEDIC AND DENTAL APPLICATIONS

[75] Inventors: George A. Graves, Jr., Bellbrook; Dale E. McCullum, Vandalia; Steven M. Goodrich, Dayton, all of Ohio

[73] Assignee: University of Dayton, Dayton, Ohio

[21] Appl. No.: 934,771

[22] Filed: Nov. 25, 1986

[51] Int. Cl.$^4$ .................. B32B 9/00; B05D 7/00; A61L 27/00; A61C 13/00

[52] U.S. Cl. ..................... 428/403; 428/404; 623/16; 106/3.5; 433/201.1; 433/212.1; 427/215

[58] Field of Search ............... 428/403, 404; 433/167, 433/201.1, 212.1, 222.1; 623/16, 16 D, 16 E, 16 G; 100/35; 501/32; 427/215

[56] References Cited

U.S. PATENT DOCUMENTS

| | | | |
|---|---|---|---|
| 3,787,900 | 1/1974 | McGee | 3/1 |
| 3,922,155 | 11/1975 | Broemer et al. | 65/33 |
| 3,929,971 | 12/1975 | Roy | 423/308 |
| 3,981,736 | 9/1976 | Broemer et al. | 106/39.6 |
| 4,097,935 | 7/1978 | Jarcho | 3/1.9 |
| 4,103,002 | 7/1978 | Hench et al. | 428/426 X |
| 4,113,500 | 9/1978 | Ebihara et al. | 106/39.5 |
| 4,120,730 | 10/1978 | Trojer et al. | 106/39.6 |
| 4,135,935 | 1/1979 | Pfeil et al. | 106/35 |
| 4,149,893 | 4/1979 | Aoki et al. | 106/35 |
| 4,149,894 | 4/1979 | Ebihara et al. | 106/39.6 |
| 4,192,021 | 3/1980 | Deibig et al. | 3/1.9 |
| 4,207,306 | 6/1980 | Jarcho | 423/633 |
| 4,218,255 | 8/1980 | Bajpai et al. | 106/45 |
| 4,222,128 | 9/1980 | Tomonaga et al. | 3/1.9 |
| 4,308,064 | 12/1981 | Takami et al. | 623/16 X |
| 4,330,514 | 5/1982 | Nagai et al. | 423/309 |
| 4,371,484 | 2/1983 | Inukai et al. | 264/44 |
| 4,376,168 | 3/1983 | Takani et al. | 501/1 |
| 4,451,235 | 5/1984 | Okunda et al. | 433/201 |
| 4,503,157 | 3/1985 | Hatahira | 501/1 |
| 4,518,430 | 5/1985 | Brown et al. | 106/35 |
| 4,542,167 | 9/1985 | Aoki | 523/109 |
| 4,548,959 | 10/1985 | Nagai et al. | 523/115 |
| 4,576,922 | 3/1986 | O'Brien et al. | 501/32 |
| 4,693,986 | 9/1987 | Vit et al. | 623/16 X |

FOREIGN PATENT DOCUMENTS 161578 11/1985 European Pat. Off. ............ 428/403

OTHER PUBLICATIONS

Graves, G. A. et al., "Resorbable Ceramic Implants," *J. Biomed. Mater. Res. Symp.* 2 (Part 1): 91, 1971.
Graves, G. A. et al., "The Influence of Compositional Variations on Bone Ingrowth of Implanted Porous Calcium Aluminate Ceramics," *J. Biomed. Mater. Symp.* 6: 17, 1975.

*Primary Examiner*—John E. Kittle
*Assistant Examiner*—Susan S. Ducker
*Attorney, Agent, or Firm*—Biebel, French & Nauman

[57] ABSTRACT

The present invention provides a ceramic composite having an open porous network and a controlled pore size comprising a plurality of ceramic particles having a fused glass coating and a method for producing the same. The ceramic particles are enveloped by and bonded to adjacent ceramic particles at their interfaces by the glass coating.

24 Claims, 3 Drawing Sheets

CONTROLLED PORE SIZE CERAMICS PARTICULARLY FOR ORTHOPAEDIC AND DENTAL APPLICATIONS

BACKGROUND OF THE INVENTION

The present invention relates to a ceramic having a controlled pore size, and more particularly, to a controlled pore structure, liquid phase sintered ceramics for orthopaedic and dental applications.

Ceramic materials which are useful as bone substitutes are used in numerous orthopaedic and dental applications including as implants. Examples of such bone substitutes are described in U.S. Pat. Nos. 4,097,935 to Jarcho; 4,113,500 to Ebihara et al; 4,149,893 to Aoki et al; and 4,330,514 to Nagai et al.

Two bone substitute materials, hydroxyapatite and tricalcium phosphate, have been approved for general dental implant use, and in some selected instances, orthopaedic clinical trials. However, these materials are only available in particulate or solid bulk closed cell forms. Thus, the use of such materials in orthopaedic and dental applications has been limited.

Bone substitutes such as hydroxyapatite have been combined with other agents in various medical applications. Surgical cements including hydroxyapatite as the bone substitute are used in numerous orthopaedic and dental applications including repairing bone fractures, in attaching bone plates and other prostheses, in bridging comminuted fractures, and in filling or aligning dental cavities. Examples of such compositions are described in U.S. Pat. Nos. 4,518,430 to Brown et al; and 4,542,167 to Aoki et al. U.S. Pat. No. 4,451,235 to Okuda et al discloses a dental root material comprising hydroxyapatite and an organic matrix such as polyethylene.

U.S. Pat. No. 4,135,935 to Pfeil et al discloses a composite material useful as an implant. A first starting material which is preferably an apatite and a second starting material which is preferably a glass are ground, preferably jointly, to a particle size preferably between about 200–500 microns. The resultant mixture is finely comminuted to a particle size preferably between about 20–50 microns. The mixture is compressed to form shaped bodies and sintered. This material does not have the open pore structure which characterizes the ceramic material of the present invention.

SUMMARY OF THE INVENTION

The present invention provides a ceramic composite having an open porous network of controlled pore size comprising a plurality of ceramic particles having a glass coating which bonds the ceramic particles at their interfaces. While the present invention is particularly directed to providing ceramics which are useful in orthopaedic and surgical applications, those skilled in the art will appreciate that the teachings herein are relevant to ceramics generally where a controlled pore size is desired. By varying the size of the ceramic particles and the thickness of the glass coating, the pore size of the composite ceramic can be varied.

Accordingly, one object of the present invention is to provide a ceramic material having a controlled pore size.

A further object of the present invention is to provide a ceramic composite having a controlled pore size comprising a plurality of particles of a bone ingrowth promoting material useful in dental and orthopaedic applications.

An additional object of the present invention is to provide a ceramic composite having a controlled pore size useful in dental and orthopaedic applications wherein the degree of resorbability can be varied.

Another object of the present invention is to provide ceramic particles having a finely divided or fused glass coating useful in providing a ceramic composite having a controlled pore size.

Still another object of the present invention is to provide a process for preparing a ceramic composite in accordance with the present invention.

Other objects and advantages of the present invention will become apparent from the following description and the appended claims.

DETAILED DESCRIPTION OF THE INVENTION

Figure 1:
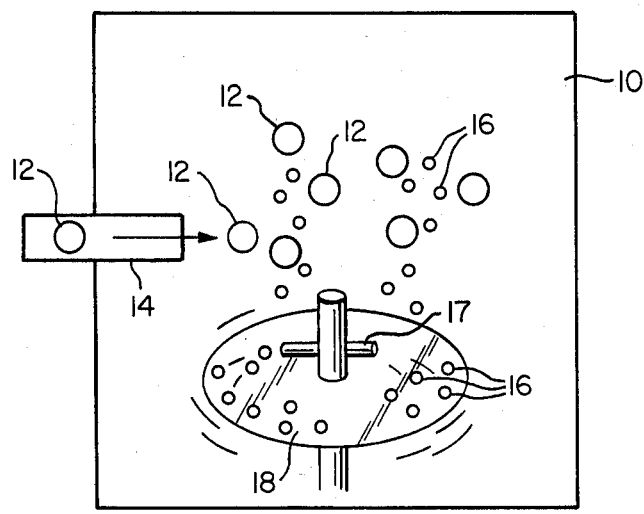
FIG. 1 illustrates an agglomerator useful in coating the ceramic particles of the present invention with a ground glass.

As stated earlier, the principal object of the present invention is to provide a ceramic composite having a controlled pore size. In order to achieve this object, the size of the ceramic particles must be controlled. Knowing the size of the ceramic particle and the thickness of the glass coating, the pore size of the ceramic material can be calculated by using the equation for closely packed particles. The ceramic particles used in the present invention typically have a particle size of less than about 2000 microns. If the particle size is larger than 2000 microns, the present invention can be used, but usually there are more expedient means available to achieve the desired pore size. The amount of glass necking is also less and the porous ceramic is not as strong. Preferably, the ceramic particles of the present invention have a size of about 100 to 1000 microns, and more preferably, 500 to 1000 microns.

Tne ceramic composite of the present invention has broad application because the ceramic particles can be any of a variety of ceramic materials. It is useful in providing bone implants, surgical cements or grouts, and drug delivery devices. Outside of the biomedical field, its open cell pore structure is useful in providing microporous filters.

Typical examples of useful ceramics are $Al_2O_3$, $MgO$, $ZrO_2$, $SiC$, etc. However, the ceramic composite of the present invention is particularly useful in dental and orthopaedic applications. Ceramic particles which are useful for such dental and orthopaedic applications are a bone ingrowth promoting material. The term "bone ingrowth promoting material" means a material, which upon implanting into the human body, will promote or aid the growth of new bone around the ceramic material. This material may function as a scaffold for bone growth and/or provide nutrients which promote bone growth.

In some applications, it is anticipated that a ceramic particle of a nonresorbable bone ingrowth promoting material would be useful. Examples of nonresorbable bone ingrowth promoting materials are hydroxyapatite, aluminum oxide, pyrolytic carbon, etc. A preferred non-resorbable bone ingrowth promoting material is hydroxyapatite. Examples of commercially available hydroxyapatite include Calcitite 2040, a nonresorbable synthetic hydroxyapatite available from Calcitek, Inc. of San Diego, Calif.; and Biogel, a hydroxyapatite produced by Bio Rads Lab of Richmond, Calif.

In other applications, the ceramic particles are a resorbable bone ingrowth promoting material. Examples of useful resorbable bone ingrowth promoting materials include various calcium aluminates, calcium phosphates, calcium aluminophosphates, and calcium sulfates. A preferred resorbable bone ingrowth promoting material is tricalcium phosphate. Specific examples of resorbable bone ingrowth promoting materials are the ALCAP (calcium aluminophosphate) ceramic described in U.S. Pat. No. 4,218,255 to Bajpai in ground or powdered form; calcium phosphates described in U.S. Pat. No. 4,192,021; and the ALCAP ceramics described by Graves, G. A., et al, "Resorbable Ceramic Implants," *J. Biomed.Mater.Res.Symp.* 2(Part I) 91(1972).

Calcium aluminophosphate ceramics useful in the present invention can be obtained by mixing calcium oxide (CaO), aluminum oxide ($Al_2O_3$), and phosphorus pentoxide ($P_2O_5$) in weight ratios of about 35 to 40% CaO, about 45 to 55% $Al_2O_3$, and about 10 to 20% $P_2O_5$; compressing the mixture; and calcining. A typical ceramic is prepared from a 38:50:12 mixture of calcium oxide, aluminum oxide, and phosphorus pentoxide which is calcined at 1300° C. for 12 hours and ground.

Resorbable and nonresorbable bone ingrowth promoting materials may be combined to provide a partially resorbable ceramic. For example, in order to stimulate bone growth, it may be desirable to formulate the composition such that a major or a minor portion of the ceramic is resorbed.

The ceramic particles of the present invention are enveloped by a fusible glass and are bonded to adjacent ceramic particles at their interfaces by the fusible glass. Any glass is useful in the ceramic material of the present invention, but preferably, a biocompatible glass having a melting point in the range of about 500° to 1000° C. is used.

In many biological applications, the fusible glass is resorbable. A particularly useful resorbable glass comprises calcium oxide (CaO) and phosphorus pentoxide ($P_2O_5$). Other ingredients such as calcium fluoride ($CaF_2$), water ($H_2O$), and other metal oxides containing cations such as magnesium, zinc, strontium, sodium, potassium, lithium, silicon, boron, and aluminum oxides may also be incorporated in small amounts. In terms of the binary mixture, the preferred Ca:P mole ratio ranges from about 0.25 to 0.33. Preferably, the glass comprises by weight 5—50% CaO, 50—95% $P_2O_5$, 0-5% $CaF_2$, 0-5% $H_2O$, and 0-10% of a metal oxide selected from the group consisting of magnesium, zinc, strontium, sodium, potassium, lithium, and aluminum oxides. In a preferred embodiment, the calcium oxide (CaO) is present by weight in the amount of 15-25%; the phosphorus pentoxide ($P_2O_5$) is present by weight in the amount of 65-90% while either calcium fluoride ($CaF_2$) or water ($H_2O$) is present by weight in the amount of 0.1-4%.

Comparable to the ceramic particles, the degree of resorbability of the glass coating can be controlled. For example, as the amount of CaO increases, the degree of resorbability decreases. Also, as the amount of $Na_2O$ increases, the degree of resorbability decreases. Additions of potassium, aluminum, or zinc oxide can also be made to achieve varying degrees of resorption in body fluids. The glass compositions can be formulated to have a range of solubility rates or be virtually insoluble.

In Table 1 below, glass compositions are provided in order of increasing resorbability:

TABLE 1

| Example | CaO | $P_2O_5$ | $Na_2O$ | $K_2O$ | $Al_2O_3$ | MgO | ZnO | $SiO_2$ |
|---------|-----|----------|---------|--------|-----------|-----|-----|---------|
| A | 10 | — | 12 | — | 1 | 3 | — | 74 |
| B | — | 58 | — | 37 | 5 | — | — | — |
| C | — | 56 | 21 | 20 | — | — | 3.0 | — |
| D | — | 63 | — | 30 | 7 | — | — | — |
| E | 20 | 80 | — | — | — | — | — | — |

In making the ceramic material of the present invention, the glass is ground to a particle size of about 10 to 50 microns and coated on the surface of the larger ceramic particles. The particle size should be as uniform as possible.

Typically the glass is adhered to the ceramic particles as a slurry in a solution of a binder such as polyvinyl alcohol (PVA). When the ceramic is subsequently sintered, the binder burns off. The coating is typically about the thickness of the glass particle, although thicker coatings may also be useful. The weight ratio of the ceramic particles to the glass coating is about 8:1 to 14:1, and, preferably about 10:1 to 12:1. In a preferred embodiment, the ratio which provides a desirable thin coating with good porosity and good necking between the ceramic particles is about 11:1. Of course, this will vary with the particle size of the ceramic.

Methods for obtaining hydroxyapatite and tricalcium phosphate particles are known in the art. Two relatively new techniques can also be used. One is sol-gel processing, a method of preparing solid materials that result when certain combinations of chemicals are mixed and precipitated from solution. The sol-gel, if dried slowly, can yield very fine grained ceramics which sinter to high density. The second is a process that provides particles of well controlled size and shape by using spray drying and agglomeration techniques which, until now, were used primarily in the food and drug industry. A slurry of the ceramic and a binder such as PVA is fed to a spray dryer (e.g., a Bowen Ceramic Spray Dryer, Bowen Engineering, Inc. Somerville, N.J.) where it is atomized into fine droplets which are rapidly dried to yield relatively uniform spheres of the ceramic which are sintered for example in a tunnel kiln. Both techniques after sintering provide dense, spherical shaped ceramic particles such as hydroxyapatite or tricalcium phosphate in controlled sizes which may be used to form the porous ceramic of the invention. These materials are also available commercially.

FIG. 1 illustrates an agglomerator 10 useful in coating the ceramic particles of the present invention with glass. Ceramic particles 12 are fed by air through tube 14 into the agglomerator 10. A slurry of a glass powder 16 in a binder is fed to a rotary disc 18 through tube 17.

As the disc 18 rotates, the glass powder 16 collides with and coats ceramic particles 12. The glass coated particles roll off the plate 18 and are dried in a hot air stream and collected. The resulting glass coated ceramic particles 20 appear as schematically illustrated in FIG. 3.

Figure 2:
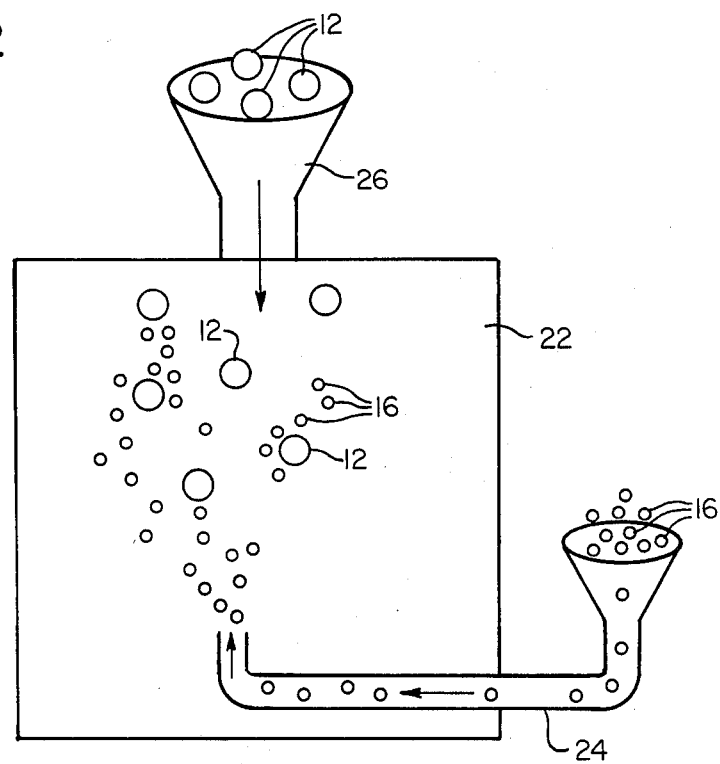
FIG. 2 illustrates a spray dryer useful in coating the ceramic particles of the present invention with a ground glass.

FIG. 2 illustrates a spray dryer 22 useful in coating the ceramic particles 12 with the glass powder slurry 16. Glass powder 16 is fed through a tube 24 into spray dryer 22. The ceramic particles 12 are dropped through tube 26 into the spray dryer 22. The ceramic particles 12 and the glass powder 16 collide and the glass powder 16 coats the ceramic particles 12 to produce the glass coated ceramic particles 20 of FIG. 3.

Figure 3:
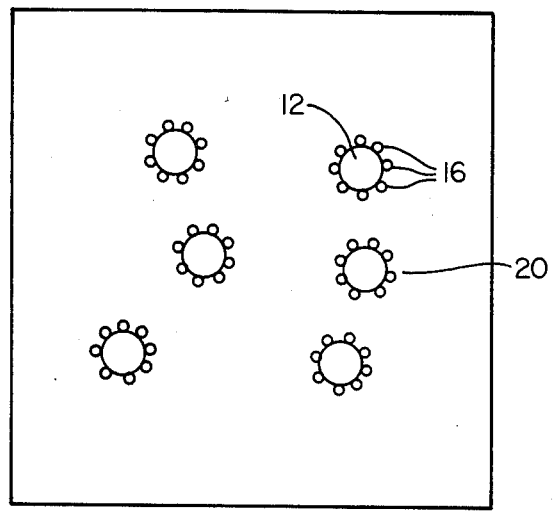
FIG. 3 illustrates the ceramic particles of the present invention with a glass powder coating prior to sintering.
Figure 4:
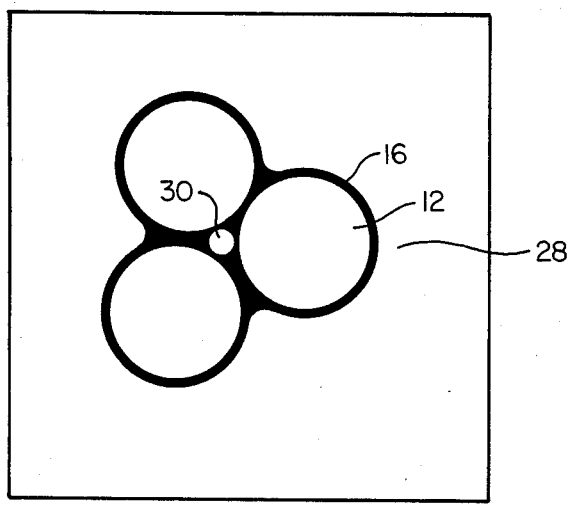
FIG. 4 illustrates a plurality of the ceramic particles of the present invention with a glass coating after liquid phase sintering.
Figure 5:
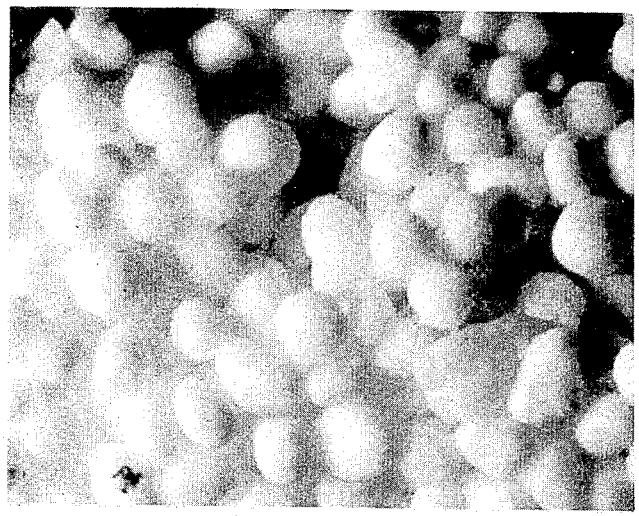
FIG. 5 is a scanning electron microscope photograph (magnification 50×) of a ceramic in accordance with the present invention showing the glass coated ceramic particles and the glass necking between them.

The glass coated ceramic particles 20 of FIG. 3 are lightly compacted into a desired shape and then sintered. The particles may be compacted in a mold under pressures of about 5 to 1000 psi. Virtually any simple shape can be produced. Upon sintering, surface tension causes the glass powder 16 to melt and flow on the surface of the ceramic particles 12 to form the ceramic material 28 of FIGS. 4 and 5. Typically, the glass coated ceramic particles 20 are sintered at temperatures of about 600° to 1200° C. (other temperatures can also be used) for about 5 to 30 minutes. The glass powder 16 envelops the ceramic particles 12 and bonds the adjacent ceramic particles 12 at their interfaces by necking between the ceramic particles 12. Pores 30 form in the ceramic material 28.

In addition to coating larger ceramic particles with a smaller fusible glass powder, other means are also envisioned for providing glass-coated ceramic particles useful in forming the porous ceramics of the present invention. In particular, ceramic particles such as HA and TCP, when formed by spray drying or agglomeration, are sintered prior to coating with glass. This sintering is usually performed by the manufacturer of commercially available materials. However, a continuous process is envisioned in which the sintered particles are fluidized and contacted with the glass powder while they are at an elevated temperature such that the glass films out directly on contact with the surface of the particle.

To promote bone ingrowth, the ceramic material of the present invention should have, or acquire through resorption, a pore size of at least about 100 microns. Including other applications, the ceramic material has a pore size of about 20 to 150 microns, and preferably, from about 100 to 150 microns.

In addition to the glass composition and the ceramic particle composition, the glass thickness is a factor in controlling the rate of resorbability of the ceramic composite. In general, for a slowly resorbable ceramic composite, the glass coating is thicker than for a faster resorbable ceramic composite.

As an example of a completely nonresorbable ceramic composite, hydroxyapatite particles can be coated with an insoluble glass such as Example A in Table 1 (a typical soda lime glass). If one then wanted to increase the resorbability of the completely nonresorbable ceramic composite, resoroable ceramic particles can be mixed with the hydroxyapatite or a resorbable glass can be used. An example of a completely resorbable ceramic composite is a tricalcium phosphate ceramic particle coated with a glass comprising CaO and $P_2O_5$ in a weight % ratio of about 20:80. Thus, the ceramic composites of the present invention have broad application because the degree and rate of resorption can be widely varied by carefully choosing the proper combination of ceramic particle composition, glass composition, and its thickness.

When selecting a ceramic particle and glass for use in the ceramic composite, tne mechanical strength of the implant and the rate of bone ingrowth should be considered. The ceramic pore size greatly influences both. Generally, a ceramic having a small pore size exhibits a high strength but a lower rate of ingrowth compared to a ceramic having a larger pore size. If the ceramic and/or glass is resorbable, the pore size will increase as the ceramic ages.

In particular, it is anticipated that a ceramic will be designed to have high strength initially until a callus has formed around the implant and become fully mineralized. By carefully designing the resorption rate of the glass and/or the ceramic particle, the implant will only be absorbed after the new bone has enough strength. Thus, the resorption rate of the ceramic typically will be less than the rate at which new bone forms.

The ceramic composites of the present invention have numerous uses in orthopaedic and dental applications. The ceramic composite may be supplied in a solid form and cut to the desired size by the practitioner. In another application, ceramic particles coated with glass powder or the fused glass powder are sold to the surgeon who would have his own furnace and mold. The mold is filled with the ceramic particles and the ceramic material in the desired shape is sintered.

Figure 6:
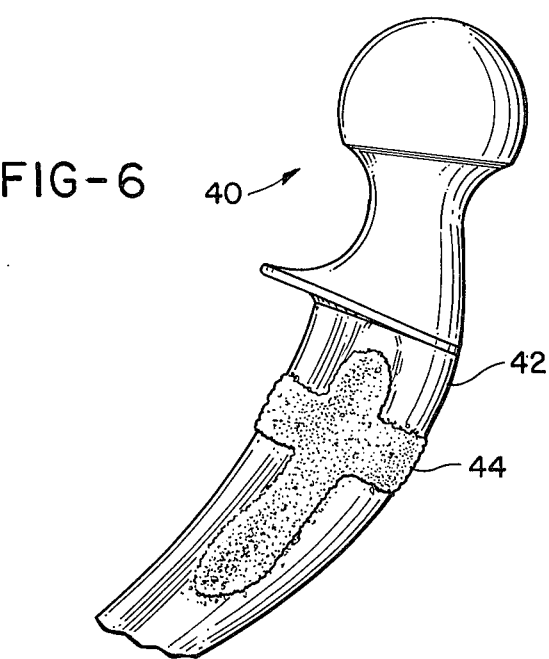
FIG. 6 illustrates a prosthesis carrying ceramic particles in accordance with the present invention.

In another application, it is anticipated that the glass coated ceramic particles could be adhered to the surface of a prosthetic device to enhance bone attachment to the device. This is accomplished by first applying a thin glass coating to the prosthesis, adhering glass coated particles to the prosthesis, and then sintering. FIG. 6 is an example of a prosthesis 40 used in hip replacements. The shank 42 of the prosthesis is driven into the bone. By applying glass-coated ceramic particles 44 to the shank, bone growth around the prosthesis and attachment of bone to the prosthesis is promoted.

The present invention is illustrated in more detail by the following non-limiting examples:

EXAMPLE 1

Approximately 2 g of a spherical particulate hydroxyapatite (HA 500, a product of Orthomatrix, Inc.) screened to 40×60 mesh was placed in a glass dish; 4 to 5 drops of a saturated solution of polyvinyl alcohol was added to the HA. The HA was coated with the PVA solution by spreading it through the solution with a spatula until it is well coated (approximately 3 to 5 minutes). The PVA coated HA was dried at 90° C. and separated with a spatula. Glass composition E (Table 1) was ground to 10-40 microns and sprinkled over the PVA coated HA. The mixture was then vibrated to uniformly coat the HA particles (approximately 1-2 minutes). The glass composition uniformly adhered to the HA particle surfaces. The glass coated HA particles were placed in a 7/32 inch die on a Clifton Hydraulic Press. Enough HA was placed in the die to displace the plunger of the die approximately ⅜ inch. 100 microliters of the PVA solution was then added to the die and the plunger was replaced and the die vibrated until the PVA solution stopped running out of the die (30-60 seconds). The press was activated and the HA particles were compacted (approximately 500 psi). The compacted cylinder was removed from the die and dried at 90° C. for appoximately 4 hours. The dried cylinder was sintered at 1000° C. for 5 minutes.

EXAMPLE 2

Hydroxyapatite was bonded to a prosthesis using the following procedure,

The prosthesis was evenly coated with a thick slurry of a glass having composition E in Table 1 using a paint brush. The slurry on the surface of the prosthesis was dried at 90° C. and glazed by heating at 1000° C. for 5 minutes. Glass coated hydroxyapatite particles were prepared as in Example 1 above and spread on the prosthesis and dried. The prosthesis was then fired at 1000° C. for 5 minutes and allowed to cool slowly.

Having described the invention in detail and by reference to preferred embodiments thereof, it will be apparent that modifications and variations are possible without departing from the scope of the invention defined in the appended claims.

What is claimed is:

1. A ceramic composite having an open porous network of a controlled pore size comprising a plurality of ceramic particles having a coating of a fused glass on their surfaces, said ceramic particles being bonded to adjacent ceramic particles at their interfaces by said fused glass coating to provide an open porous network between said ceramic particles.

2. The ceramic composite of claim 1 wherein said ceramic particles are a material selected from the group consisting of $Al_2O_3$, $MgO$, $ZrO_2$, and $SiC$.

3. The ceramic composite of claim 1 wherein said ceramic composite is useful for dental and orthopaedic implants and said ceramic particles are a bone ingrowth promoting material.

4. The ceramic composite of claim 3 wherein said ceramic particles are a nonresorbable bone ingrowth promoting material.

5. The ceramic composite of claim 4 wherein said nonresorbable bone ingrowth promoting material is selected from the group consisting of hydroxyapatite, aluminum oxide, and pyrolytic carbon.

6. The ceramic composite of claim 3 wherein said ceramic particles are a resorbable bone ingrowth promoting material.

7. The ceramic composite of claim 6 wherein said resorbable bone ingrowth promoting material is selected from the group consisting of calcium aluminate, calcium phosphates, calcium aluminophosphates, and calcium sulfates.

8. The ceramic composite of claim 7 wherein said ceramic composite has a pore size of about 20 to 150 microns.

9. The ceramic composite of claim 8 wherein said ceramic composite has a pore size of at least about 100 microns.

10. The ceramic composite of claim 9 wherein said glass is resorbable.

11. The ceramic composite of claim 10 wherein said resorbable glass comprises calcium oxide (CaO) and phosphorus pentoxide ($P_2O_5$).

12. The ceramic composite of claim 11 wherein said resorbable glass comprises by weight:

| | |
|---|---|
| CaO | 5–50% |
| $P_2O_5$ | 50–95% |
| $CaF_2$ | 0–5% |
| $H_2O$ | 0–5% |
| XO | 0–10% | wherein XO is a metal oxide selected from the group consisting of magnesium, zinc, strontium, sodium, potassium, lithium, and aluminum oxides.

13. The ceramic composite of claim 12 wherein said ceramic particles have a particle size of less than about 2000 microns.

14. The ceramic composite of claim 13 wherein said ceramic particles have a particle size of about 500 to 1000 microns.

15. The ceramic composite of claim 14 wherein the ratio of said ceramic particles to said glass coating based on the weight of said ceramic material is about 8:1 to 14:1.

16. The ceramic composite of claim 15 wherein said ceramic material is formed by coating said ceramic particles with fusible glass particles, molding said fusible glass coated ceramic particles into a desired shape, and sintering.

17. The ceramic composite of claim 16 wherein said ceramic particles are coated with said fusible glass particles in an agglomerator or a spray dryer.

18. Ceramic particles having a coating of a fused glass on the surface thereof.

19. The ceramic particles of claim 18 wherein said glass comprises calcium oxide (CaO) and phosphorus pentoxide ($P_2O_5$).

20. The ceramic particles of claim 19 wherein said particles are a bone ingrowth promoting material.

21. A process for preparing a ceramic composite having a controlled pore size comprising the steps of:
coating ceramic particles with a glass,
molding said glass coated ceramic particles into a desired shape, and
sintering.

22. The process of claim 21 wherein said glass is a fusible glass powder.

23. The process of claim 22 wherein said ceramic particles are coated with said fusible glass particles in an agglomerator or a spray dryer.

24. The ceramic composite of claim 9 wherein said glass is non-resorbable.

* * * * *